(12) United States Patent
Yaghi et al.

(10) Patent No.: US 8,735,161 B2
(45) Date of Patent: May 27, 2014

(54) GAS SENSOR INCORPORATING A POROUS FRAMEWORK

(71) Applicants: The Regents of the University of California, Oakland, CA (US); BASF SE, Ludwigshafen (DE)

(72) Inventors: Omar M. Yaghi, Berkeley, CA (US); Alexander U. Czaja, Freinsheim (DE); Bo Wang, Beijing (CN); Kosmas Galatsis, Torrance, CA (US); Kang L. Wang, Santa Monica, CA (US); Hiroyasu Furukawa, Los Angeles, CA (US)

(73) Assignees: The Regents of the University of California, Oakland, CA (US); BASF SE, Ludwigshafen (DE)

( * ) Notice: Subject to any disclaimer, the term of this patent is extended or adjusted under 35 U.S.C. 154(b) by 0 days.

(21) Appl. No.: 13/936,315

(22) Filed: Jul. 8, 2013

(65) Prior Publication Data

US 2013/0295680 A1 Nov. 7, 2013

Related U.S. Application Data

(62) Division of application No. 13/142,564, filed as application No. PCT/US2009/069700 on Dec. 29, 2009, now Pat. No. 8,480,955.

(60) Provisional application No. 61/141,200, filed on Dec. 29, 2008.

(51) Int. Cl.
*G01N 15/06* (2006.01)

(52) U.S. Cl.
USPC ........... 436/43; 422/68.1; 422/83; 422/82.01; 422/82.02; 422/82.05; 436/149; 436/164; 436/181

(58) Field of Classification Search
USPC .............. 422/50, 68.1, 82.01, 83, 98; 436/43, 436/149, 164, 181, 127, 145
See application file for complete search history.

(56) References Cited

U.S. PATENT DOCUMENTS

| | | | |
|---|---|---|---|
| 5,208,335 | A | 5/1993 | Ramprasad et al. |
| 5,648,508 | A | 7/1997 | Yaghi et al. |
| 5,733,505 | A | 3/1998 | Goldstein et al. |
| 6,501,000 | B1 | 12/2002 | Stilbrany et al. |
| 6,617,467 | B1 | 9/2003 | Muller et al. |

(Continued)

FOREIGN PATENT DOCUMENTS

| | | |
|---|---|---|
| EP | 1674555 A1 | 6/2006 |
| WO | 2004101575 A2 | 11/2004 |

(Continued)

OTHER PUBLICATIONS

Sudik et al., "Design, Synthesis, Structure, and Gas (N2, Ar, CO2, CH4 and H2) Sorption Properties of Porous Metal-Organic Tetrahedral and Heterocuboidal Polyhedra," J. Am. Chem. Soc. 127:7110-7118 (2005).

(Continued)

*Primary Examiner* — Brian J Sines
(74) *Attorney, Agent, or Firm* — Joseph R. Baker, Jr.; Gavrilovich, Dodd & Lindsey LLP

(57) ABSTRACT

The disclosure provides sensor for gas sensing including $CO_2$ gas sensors comprising a porous framework sensing area for binding an analyte gas.

15 Claims, 1 Drawing Sheet

(56) References Cited

U.S. PATENT DOCUMENTS

| | | |
|---|---|---|
| 6,624,318 B1 | 9/2003 | Mueller et al. |
| 6,893,564 B2 | 5/2005 | Mueller et al. |
| 6,929,679 B2 | 8/2005 | Muller et al. |
| 6,930,193 B2 | 8/2005 | Yaghi et al. |
| 7,196,210 B2 | 3/2007 | Yaghi et al. |
| 7,202,385 B2 | 4/2007 | Mueller et al. |
| 7,279,517 B2 | 10/2007 | Mueller et al. |
| 7,309,380 B2 | 12/2007 | Muller et al. |
| 7,343,747 B2 | 3/2008 | Muller et al. |
| 7,411,081 B2 | 8/2008 | Mueller et al. |
| 7,524,444 B2 | 4/2009 | Hesse et al. |
| 7,582,798 B2 | 9/2009 | Yaghi et al. |
| 7,652,132 B2 | 1/2010 | Yaghi et al. |
| 7,662,746 B2 | 2/2010 | Yaghi et al. |
| 7,799,120 B2 | 9/2010 | Yaghi et al. |
| 7,815,716 B2 | 10/2010 | Mueller et al. |
| 2003/0004364 A1 | 1/2003 | Yaghi et al. |
| 2003/0078311 A1 | 4/2003 | Muller et al. |
| 2003/0148165 A1 | 8/2003 | Muller et al. |
| 2003/0222023 A1 | 12/2003 | Mueller et al. |
| 2004/0081611 A1 | 4/2004 | Muller et al. |
| 2004/0225134 A1 | 11/2004 | Yaghi et al. |
| 2004/0249189 A1 | 12/2004 | Mueller et al. |
| 2004/0265670 A1 | 12/2004 | Muller et al. |
| 2005/0004404 A1 | 1/2005 | Muller et al. |
| 2005/0014371 A1 | 1/2005 | Tsapatsis |
| 2005/0124819 A1 | 6/2005 | Yaghi et al. |
| 2005/0154222 A1 | 7/2005 | Muller et al. |
| 2005/0192175 A1 | 9/2005 | Yaghi et al. |
| 2006/0057057 A1 | 3/2006 | Muller et al. |
| 2006/0135824 A1 | 6/2006 | Mueller et al. |
| 2006/0154807 A1 | 7/2006 | Yaghi et al. |
| 2006/0185388 A1 | 8/2006 | Muller et al. |
| 2006/0252641 A1 | 11/2006 | Yaghi et al. |
| 2006/0287190 A1 | 12/2006 | Eddaoudi et al. |
| 2007/0068389 A1 | 3/2007 | Yaghi et al. |
| 2007/0202038 A1 | 8/2007 | Yaghi et al. |
| 2008/0184883 A1 | 8/2008 | Zhou et al. |
| 2009/0155588 A1 | 6/2009 | Hesse et al. |
| 2010/0132549 A1 | 6/2010 | Yaghi et al. |
| 2010/0143693 A1 | 6/2010 | Yaghi et al. |
| 2010/0186588 A1 | 7/2010 | Yaghi et al. |
| 2010/0286022 A1 | 11/2010 | Yaghi et al. |
| 2011/0137025 A1 | 6/2011 | Yaghi et al. |

FOREIGN PATENT DOCUMENTS

| | | |
|---|---|---|
| WO | 2006072573 A2 | 7/2006 |
| WO | 2006116340 A1 | 11/2006 |
| WO | 2006125761 A1 | 11/2006 |
| WO | 2007054581 A1 | 5/2007 |
| WO | 2007101241 A2 | 9/2007 |
| WO | 2007111739 A2 | 10/2007 |
| WO | 2008091976 A1 | 7/2008 |
| WO | 2008138989 A1 | 11/2008 |
| WO | 2008140788 A1 | 11/2008 |
| WO | 2009020745 A2 | 2/2009 |
| WO | 2009042802 A1 | 4/2009 |
| WO | 2009056184 A1 | 5/2009 |
| WO | 2009149381 A3 | 12/2009 |
| WO | 2010083418 A1 | 7/2010 |
| WO | 2010088629 A1 | 8/2010 |
| WO | 2010090683 A1 | 8/2010 |
| WO | 2010148276 A3 | 12/2010 |
| WO | 2010148296 A3 | 12/2010 |
| WO | 2010148374 A3 | 12/2010 |
| WO | 2011014503 A1 | 2/2011 |
| WO | 2011038208 A2 | 3/2011 |

OTHER PUBLICATIONS

Tranchemontagne et al. "Metal-Organic Frameworks with High Capacity and Selectivity for Harmful Gases," Proc. Natl. Acad. Sci. USA 105:11623-11627 (2008).

Tranchemontagne et al., "Reticular Chemistry of Metal-Organic Polyhedra," Angew. Chem. Int. Ed., 2008, 47:5136-5147 (2008).

Tranchemontagne et al., "Room Temperature Synthesis of Metal-organic Frameworks: MOF-5, MOF-74, MOF-177, MOF-199, and IRMOF-0," Tetrahedron 64:8553-8557 (2008).

Tranchemontagne et al. "Secondary Building Units, Nets and Bonding in the Chemistry of Metal-Organic Frameworks," Chem. Soc. Rev. 38:1257-1283 (2009).

Uribe-Romo et al., "A Crystalline Imine-Linked 3-D Porous Covalent Organic Framework," J. Am. Chem. Soc. 131:4570-4571 (2009).

Uribe-Romo et al., "Crystalline Covalent Organic Frameworks with Hydrazone Linkages," J. Am. Chem. Soc. 133: 11478-11481 (2011).

Vairaprakash et al., "Synthesis of Metal-Organic Complex Arrays," J. Am. Chem. Soc. 133:759-761 (2011).

Valente et al., "Metal-organic Frameworks with Designed Chiral Recognition Sites," Chem. Commun. 46: 4911-4913 (2010).

Walton et al., "Understanding Inflections and Steps in Carbon Dioxide Adsorption Isotherms in Metal-Organic Frameworks," J. Am. Chem. Soc.130:406-407 (2008).

Wang et al., "Postsynthetic Covalent Modification of a Neutral Metal-Organic Framework," J. Am. Chem. Soc. 129 (41):12368-12369 (2007).

Wang et al., "Tandem Modification of Metal-Organic Frameworks by a Postsynthetic Approach," Angew. Chem. Int. 47:4699-4702 (2008).

Wang et al., "Colossal Cages in Zeolitic Imidazolate Frameworks as Selective Carbon Dioxide Reservoirs," Nature 453:207-211 (2008).

Yaghi et al., "Construction of Microporous Materials from Molecular Building Blocks," Fundamental Materials Research, T. J. Pinnavaia and M. F. Thorpe, eds., vol. II, Plenum: New York, p. 111 (1995).

Yaghi et al., "Conversion of Molecules and Clusters to Extended 3-D Cage and Channel Networks," Metal Containing Polymeric Materials, C. U. Pittman, C. E. Carraher, B. M. Culbertson, M. Zeldin, J. E. Sheets, Eds., Plenum: New York, p. 219 (1996).

Yaghi et al., "Designing Microporosity in Coordination Solids," Modular Chemistry, J. Michl, Ed., Kluwer: Boston, p. 663 (1997).

Yaghi et al., "Design of Solids from Molecular Building Blocks: Golden Opportunities for Solid State Chemistry," J. Solid State Chem. 152, 1-2 (2000).

Yaghi et al., "A Molecular World Full of Holes," Chem. Innov. p. 3 (2000).

Yaghi et al., "Reticular Synthesis and the Design of New Materials," Nature 423:705-714 (2003).

Yaghi, Omar., "Porous Crystals for Carbon Dioxide Storage," slide presentation at the Fifth Annual Conference on Carbon Capture & Sequestration, US Department of Energy on May 10, 2006 http://www.netl.doe.gov/publications/proceedings/06/carbon-seq/Tech%20Session%20193.pdf.

Yaghi et al., "Metal-Organic Frameworks: A Tale of Two Entanglements," Nature materials 6:92-93 (2007).

Yaghi, Omar, "Hydrogen Storage in Metal-Organic Frameworks," slide presentation to DOE Hydrogen Program 2007 Annual Merit Review, US Department of Energy, on May 15, 2007 at http://www.hydrogen.energy.gov/pdfs/review07/st_10_yaghi.pdf.

Yaghi et al., "Reticular Chemistry and Metal-Organic Frameworks for Clean Energy," MRS Bulletin 34:682-690 (2009).

Young, Jung Doo. International Search Report for PCT/US2010/050170. Date of Mailing: Jun. 8, 2011.

Zhao, Wei. The First Office Action for Chinese Application No. 200880003157.2. The State Intellectual Property Office of the People's Republic of China. Issue Date: Aug 5, 2011.

Zhofu et al., "A Nearly Planar Water Sheet Sandwiched between Strontium-Imidazolium Carboxylate Coordination Polymers," Inorg. Chem. 44:5200-5202 (2005).

Honda, Masashi, International Preliminary Report on Patentability for PCT/US2008/051859. Date of Issuance of the Report: Jul. 28, 2009.

Howe, Patrick. International Search Report and Written Opinion for PCT/US2009/068849. Date of Mailing of the Search Report: 04/06/201.

Howe, Patrick. International Search Report and Written Opinion for PCT/US2010/022777. Date of Mailing: Jun. 7, 2010.

(56) References Cited

OTHER PUBLICATIONS

Huang et al., "Thermal Conductivity of Metal-Organic Framework 5 (MOF-5): Part II. Measurement," Int. J. Heat Mass Transfer 50:405-411 (2007).
Isaeva et al., "Metal-organic frameworks—new materials for hydrogen storage," Russian Journal of General Chemistry 77(4):721-739(2007).
Kaderi et al., "Designed Synthesis of 3D Covalent Organic Frameworks," Science 316:268-272 (2007).
Kaye et al., "Impact of Preparation and Handling on the Hydrogen Storage Properties of Zn4O(1,4-benzenedicarboxylate)3 (MOF-5)," J. Am. Chem. Soc. 129:14176-14177 (2007).
Kim, Su Mi, International Search Report and Written Opinion for PCT/US2009/068731. Date of Mailing: Aug. 19, 2010.
Kim, Su Mi. International Search Report for PCT/US2010/039154. Date of Mailing: Feb. 23, 2011.
Kiein et al., "Combinatorial Material Libraries on the Microgram Scale with an Example of Hydrothermal Synthesis," Angew. Chemie 37(24):3369-3372 (1998).
Klaes, Daphne. International Search Report and Written Opinion for PCT/US2010/021201. Date of Mailing: Apr. 27, 2010.
Kyoungmoo et al., "A Crystalline Mesoporous Coordination Copolymer with High Microporosity," Angew. Chem. Int. Ed. 47(4):677-680 (2008).
Lai et al., "Parallel Synthesis of ZSM-5 Zeolite Films from Clear Organic-Free Solutions," Angew. Chemie 40 (2):408-411 (2001).
Lee, Ji Min. International Search Report for PCT/US2010/039284. Date of Mailing: Feb. 22, 2011.
Li et al., "A metal-organic framework replete with ordered donor-acceptor catenanes," Chem. Commun. 46:380-382 (2010).
Linder, Nora. International Preliminary Report on Patentability for PCT/US2010/022777. Date of Mailing: Aug. 11, 2011.
Long et al., "The Pervasive Chemistry of Metal-Organic Frameworks," Chem. Soc. Rev. 38:1213-1214 (2009).
Lu et al., "Synthesis and Structure of Chemically Stable Metal-Organic Polyhedra," J. Am. Chem. Soc. 131:(35) 12532-12533 (2009).
Mendoza-Cortes et al., "Adsorption Mechanism and Uptake of Methane in Covalent Organic Frameworks: Theory and Experiment," J. Phys. Chem. 114:10824-10833 (2010).
Michalitsch, Richard. International Search Report and Written Opinion for PCT/US2009/069700. Date of Mailing: May 7, 2010.
Millward et al., "Metal-Organic Frameworks with Exceptionally High Capacity for Storage of Carbon Dioxide at Room Temperature," J. Am. Chem. Soc. 127:17998-17999 (2005).
Morris et al., "Crystals as Molecules: Postsynthesis Covalent Functionalization of Zeolitic Imidazolate Frameworks," J. Am. Chem. Soc. 130:12626-12627 (2008).
Morris et al., "A Combined Experimental—Computational Investigation of Carbon Dioxide Capture in a Series of Isoreticular Zeolitic Imidazolate Frameworks," J. Am. Chem. Soc. 132:11006-11008 (2010).
Morris et al., "Postsynthetic Modification of a Metal-Organic Framework for Stabilization of a Hemiaminal and Ammonia Uptake," Inorg. Chem. 50:6853-6855 (2011).
Mulhausen, Dorothee. International Preliminary Report on Patentability for PCT/US2009/069700. Date of Mailing: Jul. 7, 2011.
Mulhausen, Dorothee. International Preliminary Report on Patentability for PCT/US2010/021201. Date of Mailing Jul. 28, 2011.
Natarajan et al., "Non-carboxylate based metal-organic frameworks (MOFs) and related aspects," Current Opinion in Solid State and Materials Science 13(3-4):46-53 (2009).
Ni et al., "Porous Metal-Organic Truncated Octahedron Constructed from Paddle-Wheel Squares and Terthiophene Links," J. Am. Chem. Soc. 127:12752-12753 (2005).
Nickitas-Etienne, Athina. International Preliminary Report on Patentability for PCT/US2008/07741. Date of issuance of this report: Mar. 30, 2010.
Nickitas-Etienne, Athina, International Preliminary Report on Patentability for PCT/US2009/068731. Date of Issuance of the Report: Jun. 21, 2011.
Nickitas-Etienne, Athina. International Preliminary Report on Patentability for PCT/US2009/068849. Date of Mailing: Jun. 30, 2011.
Oisaki et al., "A Metal-Organic Framework with Covalently Bound Organometallic Complexes," J. Am. Chem. Soc. 132:9262-9264 (2010).
Okeeffe et al., "Reticular Chemistry—Present and Future Prospects—Introduction,"J. Solid State Chem.178:V-VI (2005).
O'Keeffe et al., "The Reticular Chemistry Structure Resource (RCSR) Database of, and Symbols for, Crystal Nets," Acc. Chem. Res. 41:1782-1789 (2008).
Park, Jae Woo. International Search Report for PCT/US2010/039123. Date of Mailing: Feb. 24, 2011.
Patteux, Claudine. International Search Report for PCT/US2010/043373. Date of Mailing: Oct. 10, 2010.
Phan et al., "Synthesis, Structure, and Carbon Dioxide Capture Properties of Zeolitic Imidazolate Frameworks," Acc. Chem. Res 43:58-67 (2009).
Plevert et al., "Synthesis and Characterization of Zirconogermanates," Inorg. Chem., 42:5954-5959 (2003).
Rosi et al., "Hydrogen Storage in Microporous Metal-Organic Frameworks," Science 300:1127-1129 (2003); Featured in (1) Chemical & Engineering News magazine, May 19, 2004, and (2) Technology Research News Magazine, May 21, 2003.
Rosi et al., "Rod-Packings and Metal-Organic Frameworks Constructed from Rod-Shaped Secondary Building Units," J. Am. Chem. Soc. 127:1504-1518 (2005).
Rowsell et al., "Hydrogen Sorption in Functionalized Metal-Organic Frameworks," J. Am. Chem. Soc.126: 5666-5667 (2004).
Rowsell et al., "Metal-Organic Frameworks: A New Class of Porous Materials," Microporous Mesoporous Mater. 73:3-14 (2004).
Rowsell et al., "Strategies for Hydrogen Storage in Metal-Organic Frameworks," Angew. Chem. Int. Ed. 44: 4670-4679 (2005).
Rowsell et al., "Gas Adsorption Sites in a Large-Pore Metal-Organic Framework," Science 309:1350-1354 (2005).
Rowsell et al., "Characterization of H2 Binding sites in prototypical metal-organic frameworks by inelastic neutron scattering," J. Am. Chem. Soc. 127:14904-14910 (2005).
Rowsell et al., "Effects of Functionalization, Catenation, and Variation of the Metal Oxide and Organic Linking Units on the Low-Pressure Hydrogen Adsorption Properties of Metal-Organic Frameworks," J. Am. Chem. Soc. 128: 1304-1315 (2006).
Siberio-Perez, "Raman Spectroscopic Investigation of CH4 and N2 Adsorption in Metal-Organic Frameworks," Chem. Mater. 19:3681-3685 (2007).
Spencer et al., "Determination of the Hydrogen Absorption Sites in Zn4O(1,4-benzenedicarboxylate) by Single Crystal Neutron Diffraction," Chem. Commun. 3:278-280 (2006); Epub Dec. 6, 2005.
Stallmach et al., "NMR Studies on the Diffusion of Hydrocarbons on the Metal-Organic Framework Material MOF-5," Angew. Chem. Int. Ed. 45:2123-2126 (2006).
Stock et al., "High-Throughput Synthesis of Phosphonate-Based Inorganic-Organic Hybrid Compounds under Hydrothermal Conditions," Angew. Chemie 43(6):749-752 (2004).
Ashton, Peter R. et al., "Hydrogen-Bonded Complexes of Aromatic Crown Ethers with (9-Anthracenyl) methylammonium Derivatives" J. Am. Chem. Soc., 1997, 119 (44), pp. 10641-10651.
Carlucci, Lucia et al., "Polycatenation, polythreading and polyknotting in coordination network chemistry" Coordination Chemistry Reviews 246, 2003, pp. 247-289, Elsevier.
Chae et al., "Tertiary Building Units: Synthesis, Structure, and Porosity of a Metal-Organic Dendrimer Framework (MODF-1)," J. Am. Chem. Soc., 2001, 123, 11482-11483.
Chen et al., "Interwoven Metal-Organic Framework on a Periodic Minimal Surface with Extra-Large Pores," Science, 2001, 291, 1021-1023: Featured in Chemical and Engineering News, Feb. 21, 2001.
Chen et al., "Cu2(ATC) 6H2O: Design of Open Metal Sites in Porous Metal-Organic Crystals (ATC: 1,3,5,7-adamantane tetracarboxylate)," J. Am. Chem. Soc., 2000, 122, 11559-11560.
Han, SS et al., "Improved designs of metal-organic frameworks for hydrogen storage" Angew. Chem. Int. Ed. 2007, 46, pp. 6289-6292.

(56) References Cited

OTHER PUBLICATIONS

Howe, Patrick, International Search Report and Written Opinion, PCT/US2009/068849, European Patent Office, May 26, 2010.

Kim et al., "Assembly of Metal-Organic Frameworks from Large organic and Inorganic Secondary Building Units: New Examples and Simplifying Principles for Complex Structures," J. Am. Chem. Soc., 2001, 123, 8239-8247.

Kim, Su Mi, International Search Report and Written Opinion, Date of Mailing: Feb. 24, 2010, International Application No. PCT/US09/46463.

Li et al., "20 A [Cd4In16S35]14-Supertrahedral T4 Clusters as Building Units in Decorated Cristobalite Frameworks,"J. Am. Chem. Soc., 2001, 123, 4867-4868.

Li et al., "Ge2ZrO6F2 (H2DAB)H2O: A 4-Connected Microporous Material with "Bow Tie" Building Units and an Exceptional Proportion of 3-Rings," J. Am. Chem. Soc., 2000, 122, 12409-12410.

Li et al., "Design and Synthesis of an Exceptionally Stable and Highly Porous Metal-Organic Framework," Nature, 1999, 402, 276-279: Featured in (1) Chemical and Engineering News, Nov. 22, 1999, and (2) Science News, Nov. 20, 1999.

Li et al., "Non-interpenetrating Indium Sulfide with a Supertetrahedral Cristobalite Framework," J. Am. Chem. Soc., 1999, 121, 6096-6097.

Li et al., "Supertetrahedral Sulfide Crystals with Giant Cavities and Channels," Science, 1999, 283, 1145-1147.

Li et al., "An Open-Framework Germanate with Polycubane-Like Topology," Angew. Chem. Int. Ed., 1999, 38, 653-655.

Li et al., "Transformation of Germanium Dioxide to 4-Connected Porous Germanate Net," J. Am. Chem. Soc., 1998, 120, 10569-10570.

Li et al., "Porous Germanates: Synthesis, Structure and Inclusion Properties of Ge7O14.5F2•[(CH3)2NH2]3(H2O) 0.86," J. Am. Chem. Soc., 1998, 120, 8567-8568.

Li et al., "Establishing Microporosity in Open Metal-Organic Frameworks: Gas Sorption Isotherms for Zn(BDC) (BDC=1,4-Benzenedicarboxylate)," J. Am. Chem. Soc., 1998, 120, 8571-8572.

Li et al., "Coordinatively Unsaturated Metal Centers in the Extended Porous Framework of Zn3(BDC)3•6CH3OH (BDC = 1,4-Benzenedicarboxylate)," J. Am. Chem. Soc., 1998, 120, 2186-2187.

Loeb, SJ, "Rotaxanes as ligands: from molecules to materials" Chemical Society reviews, 2007, 36, pp. 226-235.

Moyse, Ellen, International Preliminary Report on Patentability and Written Opinion, Date of Issuance of Report: Nov. 17, 2009, International Application No. PCT/US08/006008.

Nickitas-Etienne, Athina, International Preliminary Report on Patentability and Written Opinion, Date of Issuance of Report: Jan. 19, 2010, International Application No. PCT/US08/70149.

O'Keefe et al., "Frameworks for Extended Solids: Geometrical Design Principles," J. Solid State Chem., 2000, 152, 3-20.

O'Keefe et al., "Germanate Zeolites: Contrasting the Behavior of Germanate and Silicate Structures Built from Cubic T8O20 units (T=Si or Ge)," Chem. Eur. J., 1999, 5, 2796-2801.

Park, Kyo Sung et al., "Exceptional chemical and thermal stability of zeolitic imidazolate frameworks," Proc. Natl. Acad. Sci., Jul. 5, 2006, pp. 10186-10191, vol. 103, No. 27.

Plevert et al.,"A Flexible Germanate Structure Containing 24-Ring Channels With Very Low Framework Density," J. Am. Chem. Soc., 2001, 123, 12706-12707.

Reineke et al., "Large Free Volume in Interpenetrating Networks: The Role of Secondary Building Units Exemplified by Tb2(ADB)3[(CH3)2SO]4•16[(CH3)2SO]," J. Am. Chem. Soc., 2000, 122, 4843-4844: Featured in Science Magazine, Editors Choice, Nov. 2000.

Reineke et al., "A Microporosity of Lanthanide-Organic Frameworks," Angew. Chem. Int. Ed., 1999, 38, 2590-2594.

Reineke et al., "From Condensed lanthanide Coordination Solids to Microporous Frameworks having Accessible Metal Sites," J. Am. Chem. Soc., 1999, 121, 1651-1657.

Rosi et al, "Infinite Secondary Building Units and Forbidden Catenation in Metal-Organic Frameworks," Angew. Chem. Int. Ed., 2002, 41, 294-297.

Rosi et al., "Advances in the Chemistry of Metal-Organic Frameworks," CrystEngComm, 2002, 4, 401-404.

Vodak et al., "Metal-Organic Frameworks Constructed from Pentagonal Antiprismatic and Cuboctahedral Secondary Building Units," Chem. Commun., 2001, 2534-2535.

Wong-Foy, AG et al., "Exceptional H2 saturation uptake in microporous metal-organic frameworks" J. Am. Chem. Soc., 2006, 128, pp. 3494-3495.

Yaghi et al., "Synthetic Strategies, Structure Patterns, and Emerging Properties in the Chemistry of Modular Porous Solids," Acc. Chem. Res., 1998, 31, 474-484.

Yaghi et al., "Construction of a New Open-Framework Solid from 1,3,5-Cyclohexanetricarboxylate and Zinc(II) Building Blocks," J. Chem. Soc., Dalton Trans., 1997, 2383-2384.

Yaghi et al., "A Molecular Railroad with Large Pores: Synthesis and Structure of Ni(4,4'-bpy)2.5(H2O)2(ClO4)2•1.5 (4,4'-bpy)2(H2O)," Inorg. Chem., 1997, 36, 4292-4293.

Yaghi et al., "Crystal Growth of Extended Solids by Nonaqueous Gel Diffusion," Chem. Mater., 1997, 9, 1074-1076.

Yaghi et al., "Selective Guest Binding by Tailored Channels in a 3-D Porous Zinc(II)-1,3,5-Benzenetricarboxylate Network," J. Am. Chem. Soc., 1997, 119, 2861-2868.

Yaghi et al., "Construction of Porous Solids from Hydrogen-Bonded Metal Complexes of 1,3,5-Benzenetricarboxylic Acid," J. Am. Chem. Soc., 1996, 118, 9096-9101.

Yaghi et al., "T-Shaped Molecular Building Units in the Porous Structure of Ag(4,4'-bpy) NO3," J. Am. Chem. Soc., 1996, 118, 295-296.

Yaghi et al., "Hydrothermal Synthesis of a Metal-Organic Framework Containing Large Rectangular Channels," J. Am. Chem. Soc., 1995, 117, 10401-10402.

Yaghi et al., "Open-Framework Solids with Diamond-Like Structures Prepared from Clusters and Metal-Organic Building Blocks," Mater. Res. Soc. Symp. Proc., 1995, 371, 15.

Yaghi et al., "The Utility of Polymeric Matrices in the Preparation of Single Crystals of Coordination Solids: Synthesis and Structure of CuII(1,4-C4H4N2)(C4O4)(OH2)4," J. Solid State Chem., 1995, 117, 256-260.

Yaghi et al., "Presence of Mutually Interpenetrating Sheets and Channels in the Extended Structure of Cu(4,4'-Bipyridine)Cl," Angew. Chem. Int. Ed. Engl., 1995, 34, 207-209.

Yaghi et al., "Conversion of Hydrogen-Bonded manganese(II) and zinc(II) squarate (C4O42-) molecules, Chains, and Sheets to 3-D Cage Networks," J. Chem. Soc., Dalton Trans., 1995, 727-732.

Yaghi et al., "Selective binding and removal of guests in a microporous metal-organic framework," Nature, Dec. 1995, pp. 703-706, vol. 378.

Young, Lee W., International Search Report and Written Opinion, Date of Mailing: Dec. 2, 2008, International Application No. PCT/US08/77741.

Young, Lee W., International Search Report and Written Opinion, Date of Mailing: Jan. 12, 2009, International Application No. PCT/US08/70149.

Young, Lee W., International Search Report and Written Opinion, Date of Mailing of Report: May 7, 2008, International Application No. PCT/US08/51859.

Young, Lee W., "International search Report and Written Opinion," PCT/US08/06008, United States Patent & Trademark Office, Aug. 20, 2008.

Akporiaye et al., "Combinatorial Approach to the Hydrothermal Synthesis of Zeolites," Angew. Chemie 37(5):609-611 (1998).

Baharlou, Simin. International Preliminary Report on Patentability for PCT/US2009/046463. Date of Mailing: Dec. 16, 2010.

Banerjee et al., "High-Throughput Synthesis of Zeolitic Imidazolate Frameworks and Application to CO2 Capture," Science 319:939-943 (2008).

Banerjee et al., "Control of Pore Size and Functionality in Isoreticular Zeolitic Imidazolate Frameworks and their Carbon Dioxide Selective Capture Properties," J. Am. Chem. Soc. 131:3875-3877 (2009.

(56) References Cited

OTHER PUBLICATIONS

Barman et al., "Azulene Based Metal-Organic Frameworks for Strong Adsorption of H2," Chem. Commun. 46: 7981-7983 (2010).
Barton et al., "Tailored Porous Materials," Chem. Mater. 11:2633-2656 (1999).
Bloch et al., "Metal Insertion in a Microporous Metal-Organic Framework Lined with 2,2'-Bipyridine" J. Am. Chem. Soc. 132:14382-14384 (2010).
Braun et al., "1,4-Benzenedicarboxylate Derivatives as Links in the Design of Paddle-Wheel Units and Metal-Organic Frameworks," Chem. Commun. 24:2532-2533 (2001).
Britt et al., "Highly efficient separation of carbon dioxide by a metal-organic framework replete with open metal sites," Proc. Natl. Acad. Sci. USA 106:20637-20640 (2009).
Caskey et al., "Dramatic Tuning of CO2 Uptake via Metal Substitution in a Coordination Polymer with Cylindrical Pores," JACS 130(33):10870-10871 (2008).
Caskey et al., "Selected Applications of Metal-Organic Frameworks in Sustainable Energy Technologies," Material Matters 4.4:111 (2009).
Centrone et al., "Raman Spectra of Hydrogen and Deuterium Adsorbed on a Metal-Organic Framework," Chem. Phys. Lett. 411:516-519 (2005).
Chae et al., "A Route to High Surface Area, Porosity and Inclusion of Large Molecules in Crystals," Nature427, 523-527 (2004); Featured in (1) Chemical & Engineering News magazine, Feb. 9, 2004, (2) BBC World Service, Feb. 2004, (3) New Scientist, Feb. 2004.
Chen et al., "High H2 Adsorption in a Microporous Metal-Organic Framework with Open-Metal Sites," Angew. Chem. Int. Ed. 44:4745-4749 (2005).
Chen et al., "A Microporous Metal-Organic Framework for Gas-Chomatographic Separation of Alkanes," Angew. Chem. Int. Ed. 45:1390-1393 (2006).
Cho et al., "A metal-organic framework material that functions as an enantioselective catalyst for olefin epoxidation," Chem. Comm. 24:2563-2565 (2006).
Choi et al., "Combinatorial Methods for the Synthesis of Aluminophosphate Molecular Sieves," Angew Chemie 38 (19):2891-2894 (1999).
Choi et al., "Heterogeneity within Order in Crystals of a Porous Metal Organic Framework," J. Am. Chem. Soc. 133:11920-11923 (2011).
Corma et al., "A large-cavity zeolite with wide pore windows and potential as an oil refining catalyst," Nature Letters 418:514-517 (2002).
Cote et al., "Porous, Crystalline, Covalent Organic Frameworks," Science 310:1166-1170 (2005).
Cote et al., "Reticular Synthesis of Microporous and Mesoporous 2D Covalent Organic Frameworks," J. Am. Chem. Soc. 129:12914-12915 (2007).
Czaja et al., "Industrial applications of metal-organic frameworks," Chemical Society Reviews 38(5):1284-1293 (2009).
Delgado-Friedrichs et al., "Three-Periodic Nets and Tilings: Regular and Quasiregular Nets," Acta Cryst. A59: 22-27 (2003).
Delgado-Friedrichs et al., "Three-Periodic Nets and Tilings: Semiregular Nets," Acta Cryst. A59:515-525 (2003).
Delgado-Friedrichs et al., "Reticular Chemistry: Occurrence and Taxonomy of Nets, and Grammar for the Design of Frameworks," Acc. Chem. Res. 38:176-182 (2005).
Delgado-Friedrichs et al. "What Do We Know About Three-Periodic Nets?," J. Solid State Chem. 178: 2533-2554 (2005).
Delgado-Friedrichs et al. "Three-Periodic Nets and Tilings: Edge-Transitive Binodal Structures," Acta Cryst. 62:350-355 (2006).
Delgado-Friedrichs et al., "Taxonomy of Periodic Nets and the Design of Materials," Phys. Chem. 9:1035-1043 (2007).
Deng et al., "Multiple Functional Groups of Varying Ratios in Metal-Organic Frameworks," Science 327:846-850 (2010).
Deng et al., "Robust dynamics" Nature Chem. 2:439-443 (2010).
Doonan et al., "Isoreticular Metalation of Metal-Organic Frameworks," J. Am. Chem. Soc. 131:9492-9493 (2009).
Doonan, C., "Hydrogen Storage in Metal-Organic Frameworks," Annual Merit Review Proceedings of DOE Hydrogen Program, May 22, 2009.
Doonan et al., "Exceptional ammonia uptake by a covalent organic framework," Nature Chem. 2:235-238 (2010).
Duren et al., "Design of New Materials for Methane Storage," Langmuir 20:2683-2689 (2004).
Eddaoudi et al., "Design and Synthesis of Metal-Organic Frameworks with Permanent Porosity," in Topics in Catalysis, G. A. Somorjai and J. M. Thomas, Eds., 9:105 (1999).
Eddaoudi et al., "Highly Porous and Stable Metal-Organic Framework: Structure Design and Sorption Properties," J. Am. Chem. Soc. 121:1391-1397 (2000).
Eddaoudi et al., "Modular Chemistry: Secondary Building Units as a Basis for the Design of Highly Porous and Robust Metal-Organic Carboxylate Frameworks" Acc. Chem. Res. 34:319-330 (2001).
Eddaoudi et al., "Systematic Design of Pore Size and Functionality in Isoreticular Metal-Organic Frameworks and Application in Methane Storage," Science 295:469-472 (2002): Featured in (1) Chemical and Engineering News, Jan. 21, 2002, and (2) Chemical Insight magazine, Nov. 15, 2002.
Ferragut et al., "Positronium Formation in Porous Materials for Antihydrogen Production," J. Phys. Conf. Ser. 225:1-8 (2010).
Furkawa et al., "Independent verification of the saturation hydrogen uptake in MOF-177 and establishment of a benchmark for hydrogen adsorption in metal-organic frameworks," J. Mater. Chem. 17:3197-3204 (2007).
Furukawa et al., "Control of Vertex Geometry, Structure Dimensionality, Functionality, and Pore Metrics in the Reticular Synthesis of Crystalline Metal-Organic Frameworks and Polyhedra," J. Am. Chem. Soc.130:11650-11661 (2008).
Furukawa et al., "Storage of Hydrogen, Methane, and Carbon Dioxide in Highly Porous Covalent Organic Frameworks for Clean Energy Applications," J. Am. Chem. Soc. 25:8876-8883 (2009).
Furukawa et al., "Ultra-High Porosity in Metal-Organic Frameworks," Science 239:424-428 (2010).
Glover et al., "MOF-74 building unit has a direct impact on toxic gas adsorption," J. Chem. Eng. Sci. 66:163-170 (2011).
Forster et al., "A High-Throughput Investigation of the Role of pH, Temperature, Concentration, and Time on the Synthesis of Hybrid Inorganic-Organic Materials," Angew. Chemie 44(46):7608-7611 (2005).
Goebel, Matthias, Supplemental European Search Report and Written Opinion for EP08826913. Date of Completion of Search and Written Opinion: Nov. 10, 2010.
Goebel, Matthias, Supplemental European Search Report and Written Opinion for EP08754337. Date of Completion of Search and Written Opinion: Dec. 3, 2010.
Han et al., "Covalent Organic Frameworks as Exceptional Hydrogen Storage Materials," J. Am. Chem. Soc. 130: 11580-11581 (2008).
Hayashi et al., "Zeolite A Imidazolate Frameworks," Nature Materials 6:501-506 (2007).
Hexiang et al., "Multiple Functional Groups of Varying Rations in Metal-Organic Frameworks," Science 327 (5967):846-850 (2010).

GAS SENSOR INCORPORATING A POROUS FRAMEWORK

CROSS REFERENCE TO RELATED APPLICATIONS

This application is a divisional application of U.S. application Ser. No. 13/142,564, filed on Jun. 28, 2011 (now U.S. Pat. No. 8,480,955), which is a U.S. National Stage Application filed under 35 U.S.C. §371, based upon International Application No. PCT/US09/69700, filed Dec. 29, 2009, which claims priority under 35 U.S.C. §119 from Provisional Application Ser. No. 61/141,200, filed Dec. 29, 2008, the disclosures of which are incorporated herein by reference.

STATEMENT AS TO FEDERALLY SPONSORED RESEARCH

This invention was made with Government support of Grant No. DEFG-02-08ER-15935 awarded by the Department of Energy. The Government has certain rights in this invention.

The subject matter of this application arises in part from a joint research agreement between the Regents of the University of California and BASF SE.

TECHNICAL FIELD

The disclosure provides sensor for gas sensing including $CO_2$ gas sensors comprising a porous framework sensing area for binding an analyte gas.

BACKGROUND

Developing a simple, low cost $CO_2$ sensor is a goal that continues to be attempted with limited success. Carbon dioxide is very stable and hard to catalyze into ionic groups which could then be used for simple conductometric detection. Current methods for $CO_2$ detection consist of:

(i) non-dispersive infrared (NDIR) sensors having an infrared source, a light tube, an interference (wavelength) filter, and an infrared detector. The gas is pumped or diffuses into the light tube, and the electronics measures the absorption of the characteristic wavelength of light (Advantages—Sensitivities of 20-50 PPM, selective to error less than 10% solid state giving a life-time up to 10 years; Disadvantages—Very costly, typical NDIR sensors are still in the $100-$1000 range, relatively large and bulky);

(ii) Chemical $CO_2$ gas sensors with sensitive layers based on polymer, polymer arrays, metal oxides and new nanomaterials such as nanotubes and nanowires have the principal advantage of very low energy consumption and can be reduced in size to fit into microelectronic-base systems. On the downside, short- and long term drift effects as well as a rather low overall lifetime are major obstacles when compared with the NDIR measurement principle; and (iii) other methods include optical fiber based sensors and MEMS based sensors.

SUMMARY

The disclosure provides porous, covalently linked (reticulated) materials, such as metal organic frameworks (MOFs) and covalently-linked organic frameworks (COFs) and Zeolitic imidazolate frameworks (ZIFs) as component sensors.

The disclosure provides a sensor comprising a region of a porous framework wherein the region absorbs or adsorbs a gas analyte of interest; and a transducer that converts a change in the region to a detectable property thereby measuring a gas analyte that absorbs or adsorbs to the region. In one embodiment, the transducer is an optical, mechanical or electrical transducer. In one embodiment, the region of a porous framework comprises a MOF, IRMOF, ZIF or COF. In another embodiment, a region comprising a ZIF material comprises the general structure M-L-M, wherein M comprises a transition metal and L is a linking moiety, the linking moiety comprising a structure selected from the group consisting of I, II, III, or any combination thereof:

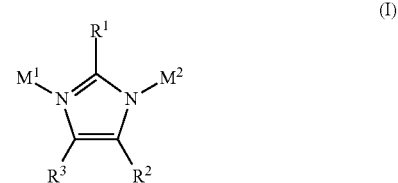

(I)

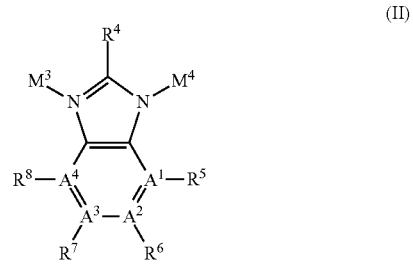

(II)

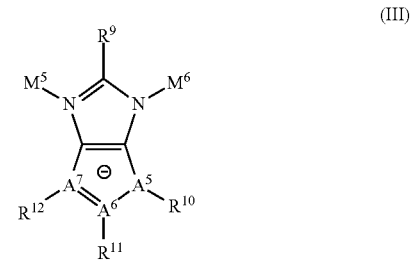

(III)

wherein A can be either C or N, wherein R5-R8 are present when A1 and A4 comprise C, wherein $R^1$, $R^4$ or $R^9$ comprise a non-sterically hindering group that does not interfere with M, wherein $R^2$, $R^3$, $R^5$, $R^6$, $R^7$, $R^8$, $R^{10}$, $R^{11}$, $R^{12}$ are each individually an alkyl, halo-cyano-nitro-, wherein when the linking group comprises structure III, R10, R11 and R12 are each individually electron withdrawing groups, wherein a gas analyte is adsorbed to the ZIF material. In one embodiment, the $R_1$, $R_4$ and $R_9$ are individually small group selected from the group consisting of H, methyl-, halo-, cyano-, and ethyl-. In another embodiment, $R_{10}$, $R_{11}$ and $R_{12}$ are each individually selected from the group consisting of a nitro-, cyano-, fluoro- and chloro-group. In yet another embodiment, L is an imidazolate or an imidazolate derivative. In one embodiment, the imidazolate or imidazolate derivative is selected from the group consisting of a substituted imidazolate; a benzimidazolate comprising a methyl-, nitro-, cyano, or chloro-group; an azabenzimidazolate; and an azabenzimidazolte wherein one or two carbon atoms on the benzimidazolate are replaced by nitrogen. In yet a further embodiment, L is selected from the group consisting of IV, V, VI, VII, VIII, and IX:

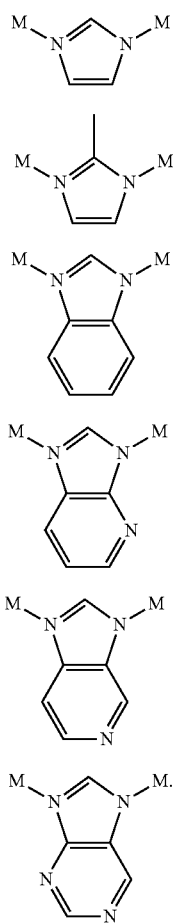

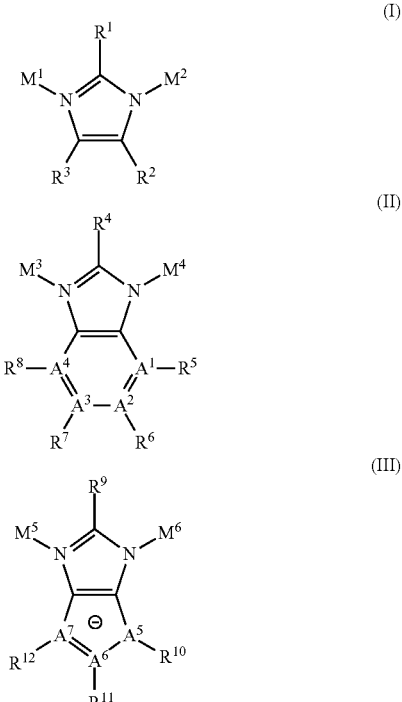

The sensor material may comprise a zeolitic framework comprising a plurality of different transition metals. For example, the transition metal can be selected from the group consisting of Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg and Uub. In yet another embodiment, the zeolitic framework comprises a plurality of different linking groups. In another embodiment, the transition metal increases the cationic charge of the zeolitic framework compared to a framework lacking a transition metal thereby increasing gas selectivity. In yet another embodiment, the sensor is a CO2 sensor. In another embodiment, the presence of an analyte (e.g., $CO_2$) is detected by optical changes, resistance changes, or mass changes in the sensing region.

The disclosure also provides a sensor array comprising a plurality of differentially responsive sensors wherein at least one sensor comprises a region of a porous framework wherein the region absorbs or adsorbs a gas analyte of interest; and a transducer that converts a change in the region to a detectable property thereby measuring a gas analyte that absorbs or adsorbs to the region. In one embodiment, the sensor array comprises a plurality of different sensors comprising different porous frameworks. In one embodiment, the array comprises a sensor having a region comprising a MOF, IRMOF, ZIF or COF. In another embodiment, a region comprising a ZIF material comprises the general structure M-L-M, wherein M comprises a transition metal and L is a linking moiety, the linking moiety comprising a structure selected from the group consisting of I, II, III, or any combination thereof:

wherein A can be either C or N, wherein R5-R8 are present when A1 and A4 comprise C, wherein $R^1$, $R^4$ or $R^9$ comprise a non-sterically hindering group that does not interfere with M, wherein $R^2$, $R^3$, $R^5$, $R^6$, $R^7$, $R^8$, $R^{10}$, $R^{11}$, $R^{12}$ are each individually an alkyl, halo-cyano-nitro-, wherein when the linking group comprises structure III, R10, R11 and R12 are each individually electron withdrawing groups, wherein a gas analyte is adsorbed to the ZIF material. In one embodiment, the $R_1$, $R_4$ and $R_9$ are individually small group selected from the group consisting of H, methyl-, halo-, cyano-, and ethyl. In another embodiment, $R_{10}$, $R_{11}$ and $R_{12}$ are each individually selected from the group consisting of a nitro-, cyano-, fluoro- and chloro-group. In yet another embodiment, L is an imidazolate or an imidazolate derivative. In one embodiment, the imidazolate or imidazolate derivative is selected from the group consisting of a substituted imidazolate; a benzimidazolate comprising a methyl-, nitro-, cyano, or chloro-group; an azabenzimidazolate; and an azabenzimidazolte wherein one or two carbon atoms on the benzimidazolate are replaced by nitrogen. In yet a further embodiment, L is selected from the group consisting of IV, V, VI, VII, VIII, and IX:

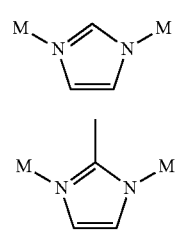

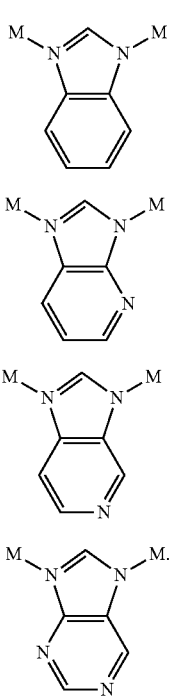

The sensor material may comprise a zeolitic framework comprising a plurality of different transition metals. For example, the transition metal can be selected from the group consisting of Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg and Uub. In yet another embodiment, the zeolitic framework comprises a plurality of different linking groups. In another embodiment, the transition metal increases the cationic charge of the zeolitic framework compared to a framework lacking a transition metal thereby increasing gas selectivity. In yet another embodiment, the sensor is a $CO_2$ sensor. In another embodiment, the presence of an analyte (e.g., $CO_2$) is detected by optical changes, resistance changes, or mass changes in the sensing region.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
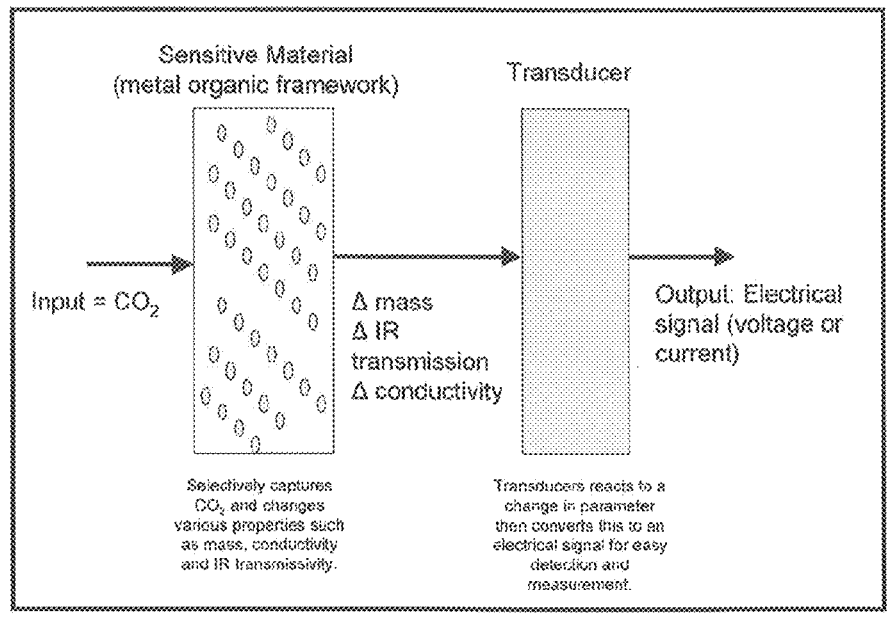
FIG. 1 is a schematic depicting a sensor process and sensing material of the disclosure.
Figure 2:
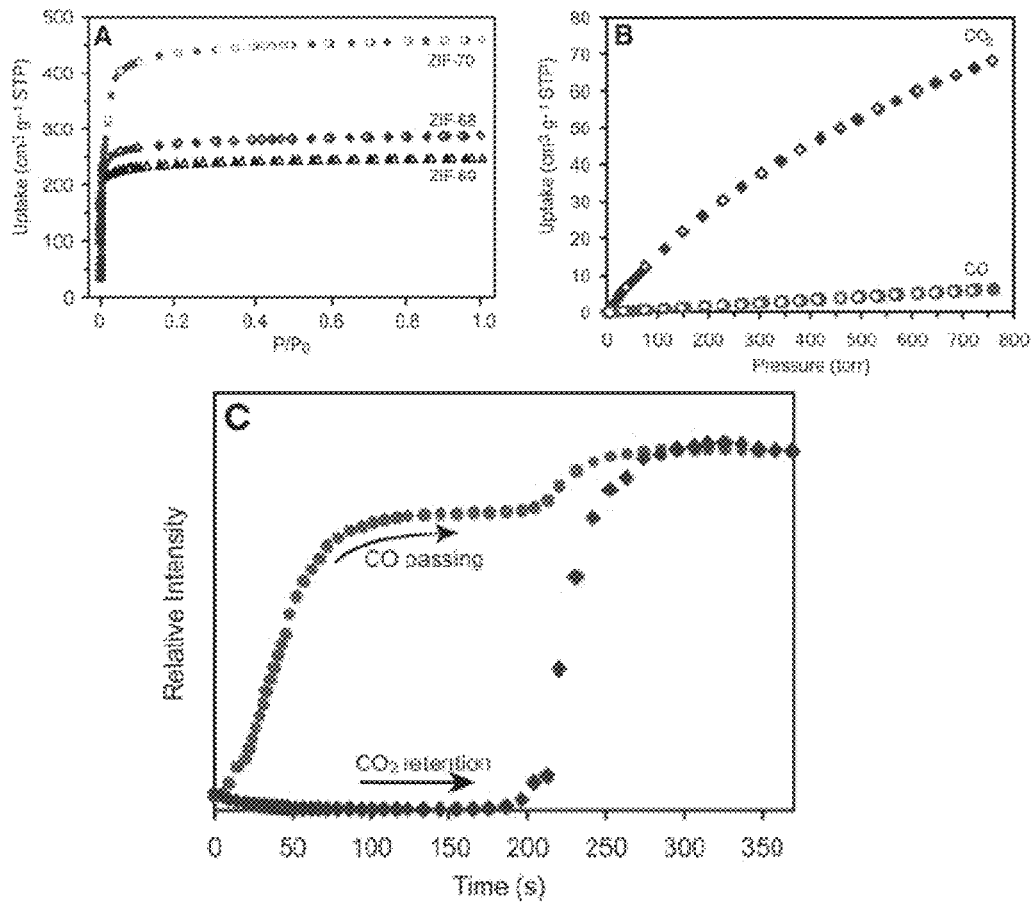
FIG. 2A-C shows gas adsorption isotherms and $CO_2$ capture properties of ZIFs. (A) The $N_2$ adsorption isotherms for heterolinked ZIF-68, 69, and 70 at 77 K. P/P0, relative pressure; STP, standard temperature and pressure. (B) The $CO_2$ and CO adsorption isotherms for ZIF-69 at 273 K. For (A) and (B), the gas uptake and release are indicated by solid and open symbols, respectively. (C) Breakthrough curves of a stream of $CO_2$/CO mixture passed through a sample of ZIF-68 showing the retention of $CO_2$ in the pores and passage of CO.

As used herein and in the appended claims, the singular forms "a," "and," and "the" include plural referents unless the context clearly dictates otherwise. Thus, for example, reference to "a sensor" includes a plurality of such sensors and reference to "the transducer" includes reference to one or more transducers and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

The approach described herein uses porous framework materials that bind to an analyte gas of interest and which upon binding to the analyte undergo a detectable change that can be measure by a transducer thereby indicating the presence of an absorbed analyte. For example, the disclosure provides porous frameworks that can be used in any number of sensor modalities comprising different transducers for measuring a detectable signal. Chemically-sensitive resistor, for example, can be used wherein the sensing region comprises a porous framework of the disclosure either alone or in combination with other conductive or non-conductive materials. Such sensors can be used in a sensing array. The change in the electrical resistance of a chemically-sensitive resistor in such a sensing array can be related to the sorption of a molecule of interest to the porous framework.

Other sensor modalities include acoustic wave, capacitance and optical transduction methods. Acoustic wave sensors measure an absorbed material by change in the vibrational frequency of the sensor (e.g., a sensor comprising a porous framework). For instance, an acoustic wave sensor may have a first vibrational frequency in the absence of a bound analyte and a second different frequency in the presence of the bound analyte. Measuring such changes in vibrational frequency can be performed in the methods and compositions of the disclosure wherein the sensor comprises a porous framework and wherein the porous framework changes mass (thus vibrational frequency) when the material binds an analyte.

Similarly, the presence of a bound analyte can be measured optically. In optical transduction modalities the optical properties are measured in the porous material prior to contact with an analyte and then subsequence to contact with the analyte. Light diffusion through a sensor material can be detected or a change in the color of the material may be detected.

Another type of sensor includes, for example, a sensor that undergoes a volume change in response to an analyte species. As the sensors are modulated in size the sensor material changes with respect to mass or optics. For example, the light diffraction indicates the presence or absence of the analyte that causes the sensing material to change. In this embodiment, the sensor material comprises a porous sensor material (e.g., a MOF, IRMOF, COF, ZIF or a combination thereof) that can be specifically functionalized for binding an analyte of interest either reversibly or irreversibly.

Yet another type of sensor includes those wherein the sensors produce a spectral recognition patterns when an analyte is present. In this embodiment the porous sensor material changes in optical properties, whether by density or through a change in emission, excitation or absorbance wavelengths.

Any number of sensor combinations comprising a porous framework of the disclosure or any number of transduction modalities can be used. For example, each individual sensor can provide a signal (e.g., a transduced signal indicative of the presence of an analyte) or a plurality of signals from an array of sensors can be used to identify an analyte of interest in a fluid. The signal transduction mechanism through which the analyte or molecule produces a signal is potentially quite broad. These include arrays of surface acoustic wave devices, quartz crystal micro-balances, dye-coated fiber optics, resistometric, electrochemical, and others modalities readily identifiable to those skilled in the art. Accordingly, transduction mechanisms include, for example optical, electrical, and/or resonance.

By "differentially responsive sensors" is meant any number of sensors comprising a porous framework that respond (e.g., transducer a signal) to the presence or interaction of an analyte with the sensor. Such measurable changes include changes in optical wavelengths, transparency of a sensor, resonance of a sensor, resistance, diffraction of light and/or sound, and other changes easily identified to those skilled in the art.

The disclosure provides sensors comprising a metal organic framework (MOF), an iso-reticular metal organic framework (IRMOF), a covalent organic framework (COF), a zeolitic inorganic framework (ZIF) or any combination thereof (referred to herein as a "porous sensor material"). MOFs, IRMOFs, COFs, and ZIFs are porous frameworks that can be functionalized to bind and interact with various analytes including, but not limited to, ammonia, carbon dioxide, carbon monoxide, hydrogen, amines, methane, oxygen, argon, nitrogen, argon, organic dyes, polycyclic organic molecules, and combinations thereof. Such sensors include, for example, chemically-sensitive resistor wherein the MOF, IRMOF, COF, and/or ZIF composition (porous sensor material) is disposed between conductive leads and undergoes a change in resistance when the porous material adsorbs or absorbs an analyte. The change in the electrical resistance between the leads can be related to the sorption of an analyte to the porous sensor material.

The diversity of the sensors of the disclosure comprising a porous framework material can be increased by combining the framework with additional material (e.g., conductive polymers, insulators and the like).

In one embodiment, the disclosure provides a sensing platform comprising a sensing region of a metal organic frameworks (MOF). The framework is a highly porous nanostructure that readily adsorb/desorb an analyte which can be sensed via various transducing methods.

Metal-organic frameworks (MOFs) are a class of crystalline porous materials whose structure is composed of metal-oxide units joined by organic linkers through strong covalent bonds. MOF materials are porous, crystalline solids. They are composed of metal-coordination-polyhedra (SBUs) and ligands (linking moieties). The ligands are at least bidentate to allow the formation of a one-, two- or three-dimensional extended structure (e.g., a teraphthalic acid or imidazol). The coordination-polyhedron can contain one or more than one metal ions (e.g., $Zn_4O$-cluster or $Cu_2$-paddlewheel). MOFs are described in more detail elsewhere herein.

The flexibility with which these components can be varied has led to an extensive class of MOF structures with ultra-high surface areas, far exceeding those achieved for porous carbons. MOFs exhibit high thermal stability, with decomposition between 350° C. and 400° C. in the case of MOF-5 (Eddaoudi M, et al., Science 295:469-472, 2002), ensuring their applicability across a wise temperature range. The unprecedented surface area and the control with which their pore metrics and functionality can be designed provides limitless potential for their structure to be tailored to carry out a specific application.

The ZIF family of materials follows the same building principles but the ligands are chose from organic molecules with imidazolate moieties (e.g., imdazolate, benzimidazolate, adenine, cytosine and so on), the metal coordination polyhedra typically contains one metal ion (e.g., Zinc(II)) and is a tetrahedron. These materials resemble topologies found in inorganic zeolites and are able to generate topologies which were not yet observed in inorganic zeolites. One feature that makes this class of material a useful sensor composition is its stability towards a vast variety of solvents, including water, and its stability even under harsh conditions (e.g., hot NaOH-solution (8M NaOH(aq))).

A zeolitic frameworks can comprise a network of homogenous transition metal or heterogeneous transition metals linked by a homogenous or heterogeneous linking moiety. The zeolitic frameworks of the disclosure can comprise any of the networks currently defined in the Atlas of Zeolite Structure Types known in the literature as well as POZ. The zeolitic frameworks of the disclosure provide nanoporous structure useful for filtration, gas storage and the like, as more fully described herein.

The disclosure also provide a general synthesis of structures having zeolite framework topologies in which all tetrahedral atoms are transition metals, and the linking moieties comprise organic linkers comprising nitrogen, sulfur or oxygen organic molecules (e.g., such as imidazolate (IM) units). The organic linkers may be further functionalized to modify the cage size and pore size or specificity to a guest species or gas molecule.

Zeolitic frameworks comprise the general structure M-L-M, wherein M comprises a transition metal and L is a linking moiety, wherein the framework is selected from the group consisting of:

(a) M-L-M, wherein L comprises structure I, II, or III; and (b) M-L-M, wherein at least one L is structure II or III and at least one other L is a structure I, II or a combination thereof:

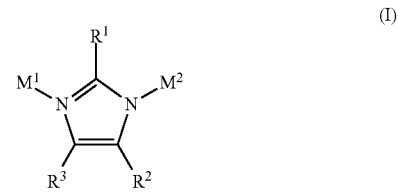

(I)

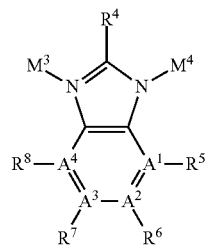

(II)

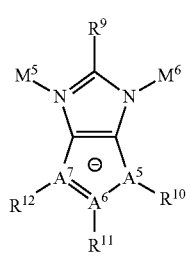

(III)

wherein A can be either C or N, wherein $R^5$-$R^8$ are present when $A^1$ and $A^4$ comprise C, wherein $R^1$, $R^4$ or $R^9$ comprise a non-sterically hindering group that does not interfere with M, wherein $R^2$, $R^3$, $R^5$, $R^8$, $R^{10}$, $R^{11}$, $R^{12}$ are each individually an alkyl, halo-cyano-nitro-, wherein when the linking moiety comprises structure III, $R^{10}$, $R^{11}$ and $R^{12}$ are each individually electron withdrawing groups, and wherein one of $R^6$ and $R^7$ comprise an electron withdrawing group.

In one embodiment, $R^1$, $R^4$ or $R^9$ comprise a non-sterically hindering electron donating group that does not interfere with M. The $R^1$, $R^4$ or $R^9$ functionalized with a group selected to interact with a particular gas or substrate. In another embodiment, $R^2$, $R^3$, $R^6$, $R^7$, or $R^{11}$ are individually H or a small electron withdrawing group. In one embodiment, the small electron withdrawing group is of sufficient size to increase a cage size for a ZIF of the disclosure. For example, $R^7$ can be a chloro-group.

In a further embodiment the imidazolate or imidazolate derivative is selected from the group consisting of IV, V, VI, VII, VIII, and IX:

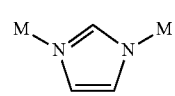

IV

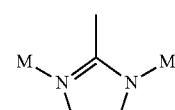

V

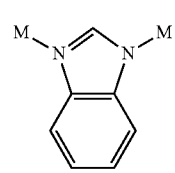

VI

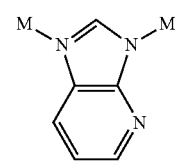

VII

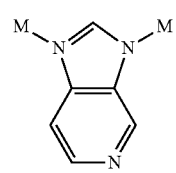

VIII

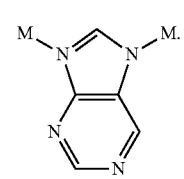

IX

In one embodiment, the imidazolate or imidazolate derivative is selected from the group consisting of a substituted imidazolate; a benzimidazolate comprising a methyl-, nitro-, cyano, or chloro-group; an azabenzimidazolate; and an azabenzimidazolate wherein one or two carbon atoms on the benzimidazolate are replaced by nitrogen. The transition metal is selected from the group consisting of Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg and Uub. In one embodiment, a zeolitic framework comprises a heterogeneous combination of transition metals. In yet another embodiment, the zeolitic framework comprises homogenous transition metal but a heterogeneous combination of linking moieties. In a further embodiment, a zeolitic framework comprises a heterogeneous mixture of transition metals and linking moieties.

In yet another embodiment, the linking moiety comprises a benzimidazolate (bIM) functionalized at the 5 or 4 and 5 positions to modify the pore character and/or cage structure of the framework. The functionalization moiety is used to increase the IM girth and comprises a small electron withdrawing group. The functionalization moiety can comprise, for example, a chloro-, bromo-, iodo-, or fluoro-containing group. For example, the disclosure provides a 5-chlorobenzimidazolate (cbIM) linked to a transition metal selected from the group consisting of Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg and Uub. In one embodiment, the cbIM linking moiety is linked to a Zn or Co transition metal.

In one embodiment, the imidazolate or imadazolate derivative linking moiety (metal groups not depicted) has a structure selected from the group consisting of:

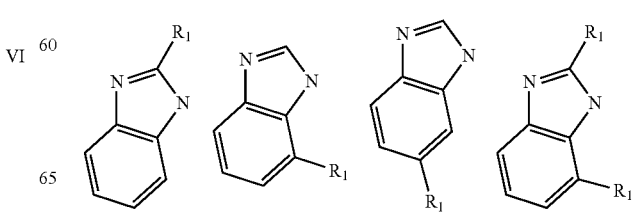

-continued

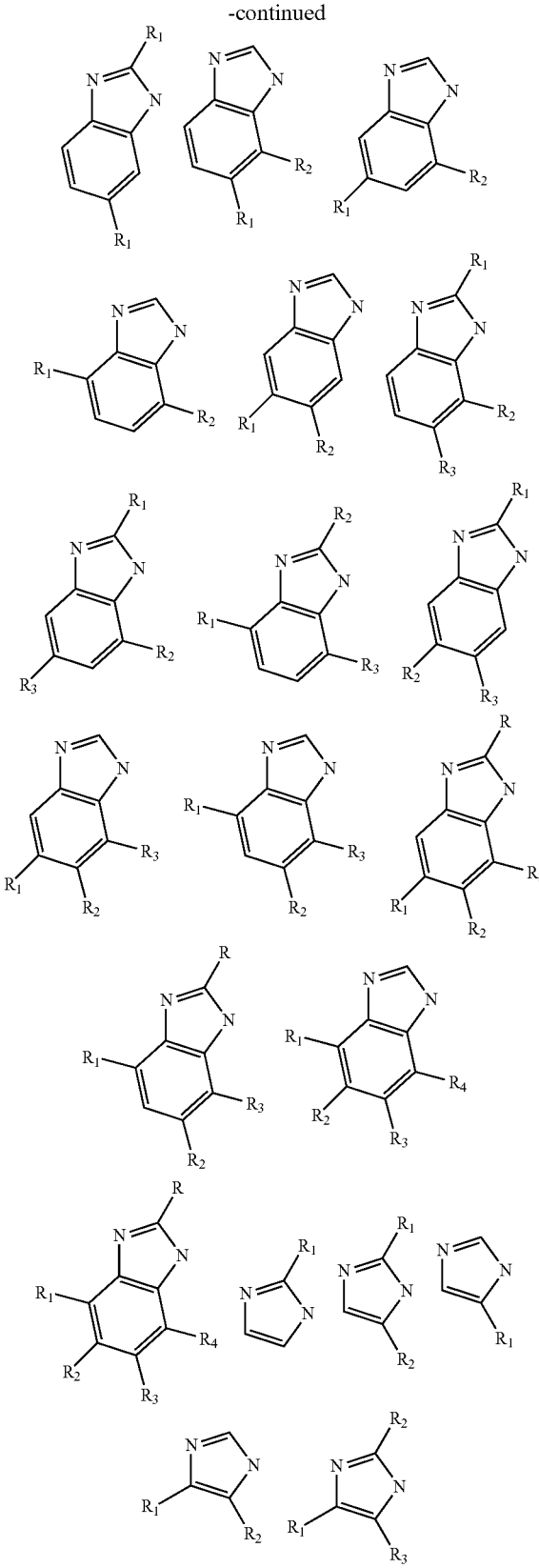

An isoreticular metal-organic framework (IRMOF) according to the disclosure comprises a plurality of secondary building units (SBUs), each of the plurality of SBUs com-prises, for example, an $M_4O(CO_2)_6$ cluster. A compound links adjacent SBUs, the linking compound comprising a linear ditopic carboxylate having at least one phenyl group and at least one functional group X attached to at least one phenyl group. The IRMOF formed has substantial permanent porosity and is very stable, with or without the presence of guest molecules.

M in the SBU is a metal cation. For example, the metal cation can be selected from the group consisting of a beryllium, zinc, cadmium, mercury, and any of the transition metals (in the periodic table, scandium through copper, yttrium through silver, lanthanum through gold, and all known elements from actinium on).

Particularly the MOF or IRMOF comprises a reactive side group, X, that can bond (either covalently, ionically or through hydrogen bonds with a gas analyte). In one embodiment the reactive side group is a Lewis Acid or base group.

Coordinatively unsaturated metal sites (e.g., MOF-74 and MOF-199) and amino functionality (e.g., IRMOF-3) prove effective in adsorbing analytes that interact strongly with those groups. For example, MOF-199 demonstrates efficacy equal to or greater than BPL-carbon against all gases and vapors tested except chlorine. It is particularly effective in removing gases that are vexing for activated carbons such as ammonia and ethylene oxide.

It is clear that a successful MOF-based dynamic adsorption medium will contain some reactive functionality, often in the form of a coordinatively unsaturated metal site. A variety of MOFs with reactive functionality in the pores is known; and there exists immense potential for the development of new MOFs with untested functionalities and metals. Furthermore, the performance of any MOF stands to be improved dramatically once it is impregnated with reactive ions and compounds.

Such porous covalently linked (reticulated) materials have in common that the properties of the pores can be precisely tuned to match the prerequisites for a given analyte. Tuneable properties include, but are not limited to, pore size, pore volume, polarity, magnetic properties, chemical environment (e.g., functional groups, metal coordination sites), and geometry of binding sites (e.g., introducing pockets for the analyte and the like.

Carbon dioxide, for example, as an analyte, interacts selectively with the ions of the SBU or with functional groups on the linker (e.g., $NH_2$). This interaction is selective or can be designed to be selective for one analyte versus another. For example, the $CO_2$ may be selectively absorbed or adsorbed to a porous framework of the disclosure while other analytes (e.g., CO, $N_2$, $O_2$, NO, $NO_2$, Ar, $C_xH_y$, benzene and the like) are not. For example, ZIF-69 is selective for capture of carbon dioxide. Such behaviour has relevant applications as a very specific and sensitive $CO_2$ sensor.

Generally, a useful sensing material comprising an organic frameworks of the disclosure have the general structure M-L-M, wherein L is a linking moiety and M are transition metals or mono- or poly-dentate groups capable of linking to at least one other linking moiety. The disclosure takes advantage of the modification of exposed side-group on a linking moiety (in some embodiments post synthesis), that can be reactive with an analyte of interest or functionalized by, for example, a post frame work reactant under suitable reaction conditions.

As used herein, a "core" refers to a repeating unit or units found in a framework. Such a framework can comprise a homogenous repeating core or a heterogeneous repeating core structure. A core comprises a transition metal or cluster of transitions metals and a linking moiety. A plurality of cores linked together defines a framework.

The term "cluster" refers to identifiable associations of 2 or more atoms. Such associations are typically established by some type of bond-ionic, covalent, Van der Waal, and the like.

A "linking cluster" refers to a one or more reactive species capable of condensation comprising an atom capable of forming a bond between a linking moiety substructure and a metal group or between a linking moiety and another linking moiety. Examples of such species are selected from the group consisting of a boron, oxygen, carbon, nitrogen, and phosphorous atom. In some embodiments, the linking cluster may comprise one or more different reactive species capable of forming a link with a bridging oxygen atom. For example, a linking cluster can comprise $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, $CH(OH)_2$, $C(OH)_3$, $CH(CN)_2$, and $C(CN)_3$, wherein R is an alkyl group having from 1 to 5 carbon atoms, or an aryl group comprising 1 to 2 pheny rings.

The term "covalent organic polyhedra" refers to a non-extended covalent organic network. Polymerization in such polyhedra does not occur usually because of the presence of capping ligands that inhibit polymerization. Covalent organic polyhedra are covalent organic networks that comprise a plurality of linking clusters linking together multidentate cores such that the spatial structure of the network is a polyhedron. Typically, the polyhedra of this variation are 2 or 3 dimensional structures.

A "linking moiety" refers to a mono-dentate or polydentate compound that bind a transition metal or a plurality of transition metals, respectively. Generally a linking moiety comprises a substructure covalently linked to an alkyl or cycloalkyl group, comprising 1 to 20 carbon atoms, an aryl group comprising 1 to 5 phenyl rings, or an alkyl or aryl amine comprising alkyl or cycloalkyl groups having from 1 to 20 carbon atoms or aryl groups comprising 1 to 5 phenyl rings, and in which a linking cluster (e.g., a multidentate function groups) are covalently bound to the substructure. A cycloalkyl or aryl substructure may comprise 1 to 5 rings that comprise either of all carbon or a mixture of carbon with nitrogen, oxygen, sulfur, boron, phosphorus, silicon and/or aluminum atoms making up the ring. Typically the linking moiety will comprise a substructure having one or more carboxylic acid linking clusters covalently attached.

As used herein, a line in a chemical formula with an atom on one end and nothing on the other end means that the formula refers to a chemical fragment that is bonded to another entity on the end without an atom attached. Sometimes for emphasis, a wavy line will intersect the line.

In one embodiment, the linking moiety substructure is selected from any of the following:

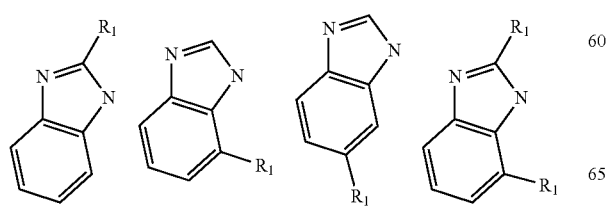

-continued

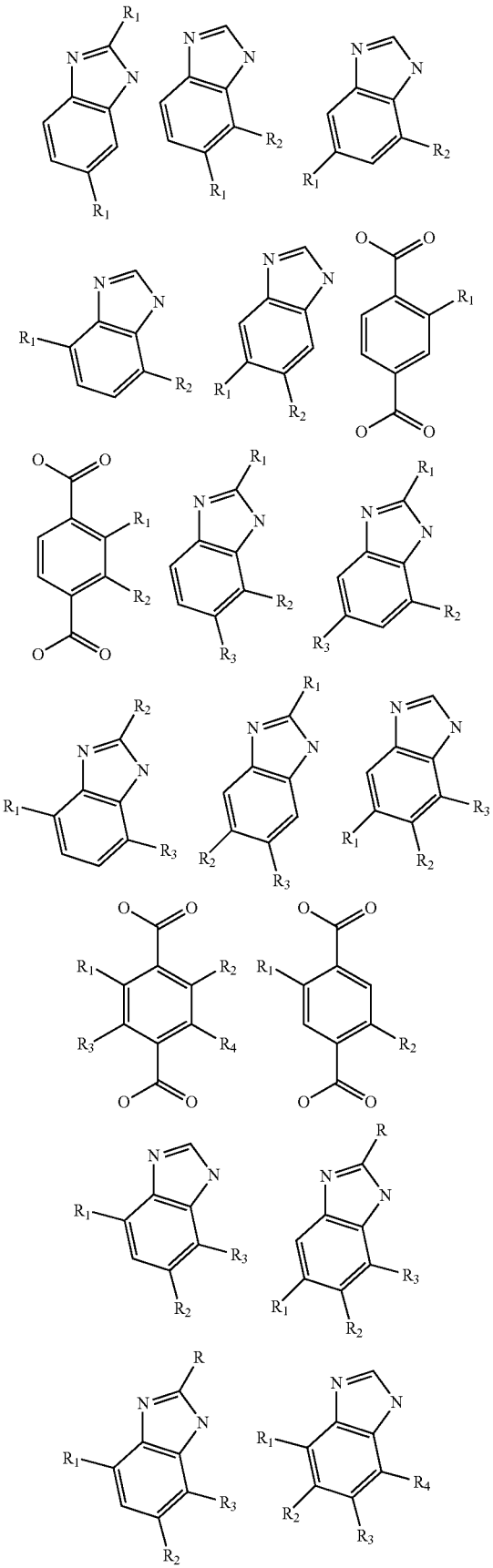

-continued

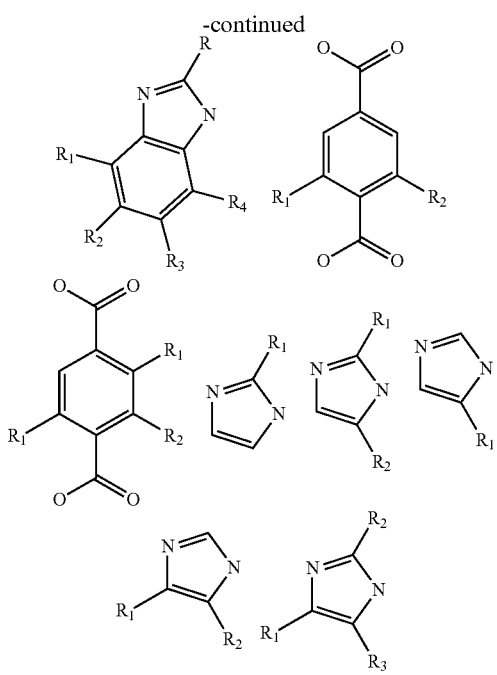

wherein $R_1$, $R_2$, $R_3$, $R_4$=$NH_2$, CN, OH, =O, =S, SH, P, Br, CL, I, F,

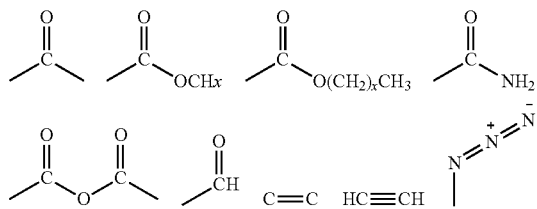

wherein X=1, 2, or 3. Further examples of ZIFs, MOFs, COFs and BOFs are set forth herein.

In one embodiment, the linking moiety of the disclosure can comprise substituted or unsubstituted aromatic rings, substituted or unsubstituted heteroaromatic rings, substituted or unsubstituted nonaromatic rings, substituted or unsubstituted nonaromatic heterocyclic rings, or saturated or unsaturated, substituted or unsubstituted, hydrocarbon groups. The saturated or unsaturated hydrocarbon groups may include one or more heteroatoms. For example, the linking moiety substructure can comprise Formula XI:

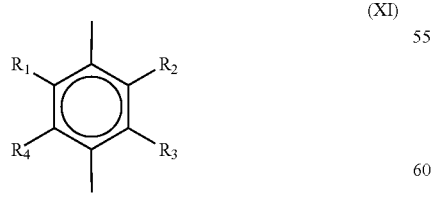

(XI)

wherein $R_1$, $R_2$, $R_3$, and $R_4$ are each independently H, alkyl, aryl, OH, alkoxy, alkenes, alkynes, phenyl and substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorus-containing groups, carboxylic acids, or esters.

In one embodiment, the linking group comprises a structure selected from the group consisting of:

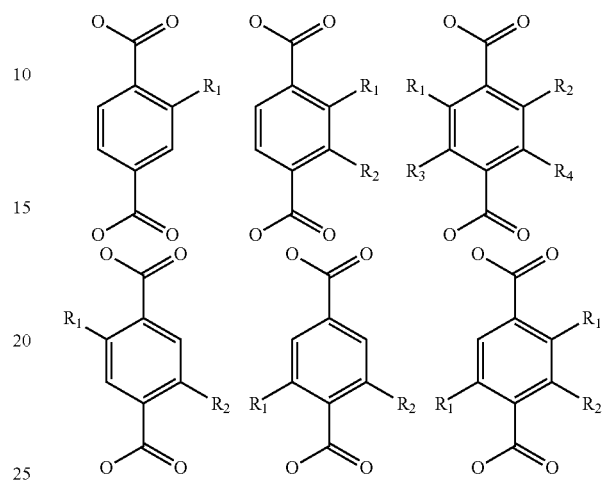

wherein the carboxylic acid groups above undergo a condensation with a transition metal to form a framework and wherein $R_1$, $R_2$, $R_3$, $R_4$=$NH_2$, CN, OH, =O, =S, SH, P, Br, CL, I, F,

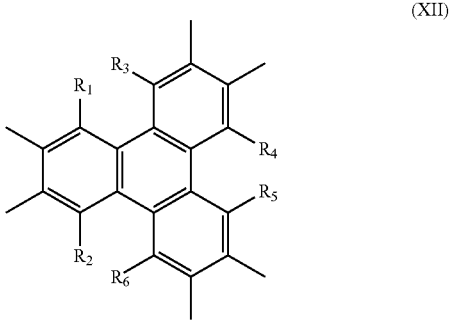

wherein X=1, 2, or 3.

In another variation of the linking moiety is described by Formula XII:

(XII)

wherein $R_1$, $R_2$, $R_3$, $R_4$, $R_5$, and $R_6$ are each independently H, alkyl, aryl, OH, alkoxy, alkenes, alkynes, phenyl and substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorus-containing groups, carboxylic acids, or esters. In one embodiment, $R_1$, $R_2$, $R_3$, $R_4$ are each independently selected from the group consisting of $NH_2$, CN, OH, =O, =S, SH, P, Br, CL, I, F,

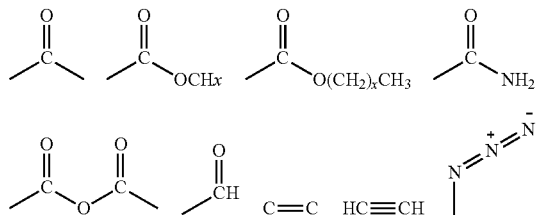

wherein X=1, 2, or 3.

In another variation the linking moiety is described by Formula XIII-XVI:

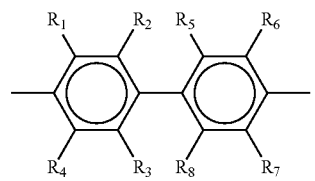
(XIII)

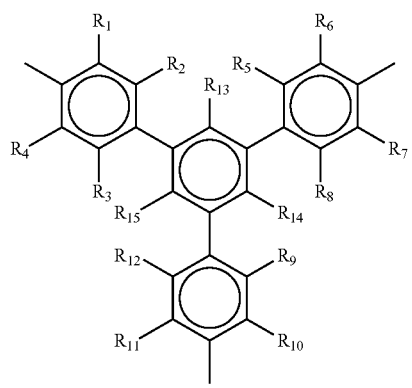
(XIV)

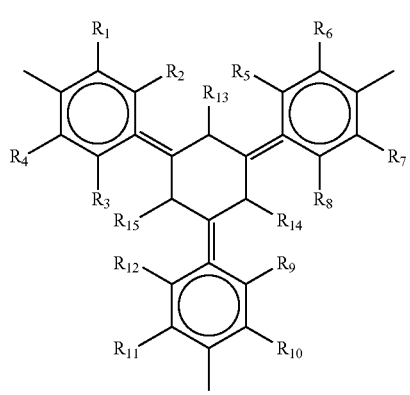
(XV)

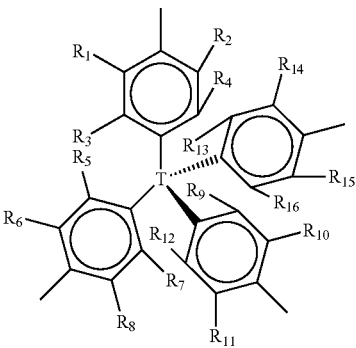
(XVI)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are each independently H, alkyl, aryl, OH, alkoxy, alkenes, alkynes, phenyl and substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorus-containing groups, carboxylic acids, or esters and T is a tetrahedral atom (e.g., carbon, silicon, germanium, tin) or a tetrahedral group or cluster. In one embodiment, $R_1$, $R_2$, $R_3$, $R_4$ are each independently selected from the group consisting of $NH_2$, CN, OH, =O, =S, SH, P, Br, CL, I, F,

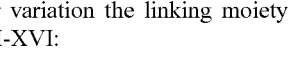

wherein X=1, 2, or 3.

In another variation the linking moiety is described by Formula XVII:

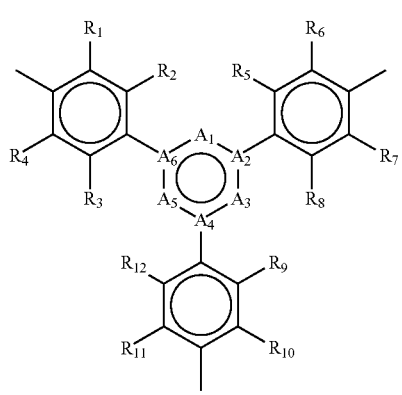
(XVII)

wherein $A_1$, $A_2$, $A_3$, $A_4$, $A_5$, and $A_6$ are each independently absent or any atom or group capable of forming a sable ring structure and $R_1$, $R_2$, $R_3$, $R_4$, $R_5$, $R_6$, $R_7$, $R_8$, $R_9$, $R_{10}$, $R_{11}$, and $R_{12}$ are each independently H, alkyl, aryl, OH, alkoxy, alkenes, alkynes, phenyl and substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorus-containing groups, carboxylic acids, or esters. In one embodiment, $R_1$, $R_2$, $R_3$, $R_4$ are each independently selected from the group consisting of $NH_2$, CN, OH, =O, =S, SH, P, Br, CL, I, F,

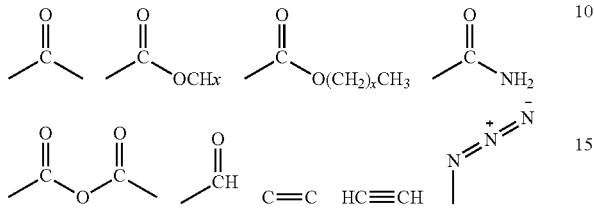

wherein X=1, 2, or 3. Specific examples of Formula XVII are provided by Formulae XVIII and XIX and ammonium salts of the linking groups of Formulae XVIII and XIX:

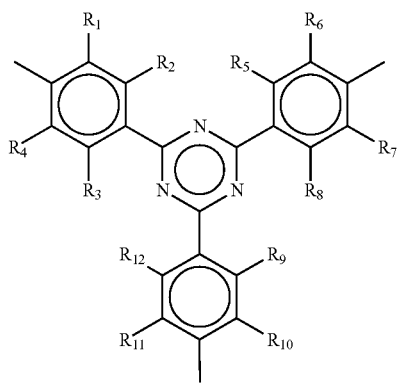

(XVIII)

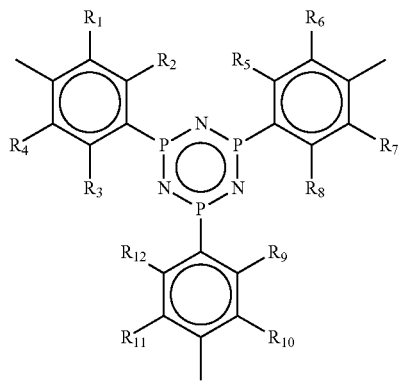

(XIX)

wherein $R_1$, $R_2$, $R_3$, $R_4$, $R_5$, $R_6$, $R_7$, $R_8$, $R_9$, $R_{10}$, $R_{11}$, and $R_{12}$ are each independently H, alkyl, aryl, OH, alkoxy, alkenes, alkynes, phenyl and substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorus-containing groups, carboxylic acids, or esters. In one embodiment, $R_1$, $R_2$, $R_3$, $R_4$ are each independently selected from the group consisting of $NH_2$, CN, OH, =O, =S, SH, P, Br, CL, I, F,

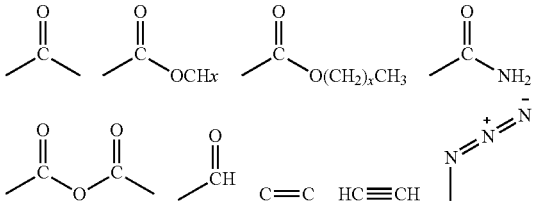

wherein X=1, 2, or 3.

In yet another variation the linking moiety is described by Formula XX:

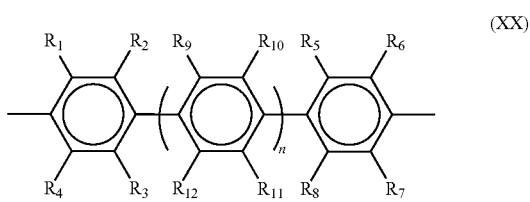

(XX)

wherein $R_1$ through $R_{12}$ are each independently H, alkyl, aryl, OH, alkoxy, alkenes, alkynes, phenyl and substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorus-containing groups, carboxylic acids, or esters; and n is an integer greater than or equal to 1. In one embodiment, $R_1$, $R_2$, $R_3$, $R_4$ are each independently selected from the group consisting of $NH_2$, CN, OH, =O, =S, SH, P, Br, CL, I, F,

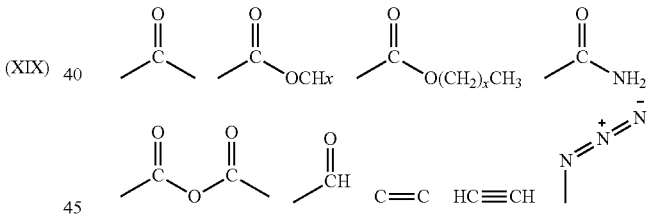

wherein X=1, 2, or 3.

The interaction of the analyte with the framework results in the change of the physical properties of the material. Changes can be observed in mass, conductivity, optical properties and magnetic properties (see, e.g., FIG. 1). For example, the mass of a MOF increases as more $CO_2$ is captured. For instance, ZIF-69 can hold up to 12 weight percent of $CO_2$ at room temperature and $pCO_2$=1 bar. This represents an increase in mass of nearly 90 grams. Such changes represent an extremely large signal change to gravimetric sensors that have sensitivity in the nanograms and pictogram ranges.

Optical properties of $CO_2$ absorption can be detected by infrared radiation. For example, $CO_2$ absorbs infrared wavelength radiation at 1.4 microns. Therefore by passing IR radiation through a porous framework of the disclosure a signal that is inversely proportional to $CO_2$ concentration can be obtained.

Conductivity measurements can also be used in the sensors of the disclosure. For example, capture of $CO_2$ within the metal organic framework alters the electronic properties of the framework. Due to $CO_2$ increasing the density of the material and enabling electron carrier transport and aggregate conductivity of a MOF increases.

A porous material of the disclosure is used as the sensing material either alone or as a combination with inorganic materials, organic materials, conductive materials (e.g., inorganic conductors or organic conductors), polymers (e.g., conductive or non-conductive polymers). The porous materials (e.g., MOF material) of the disclosure can be combined with other materials for purposes of sensing as mixtures or suspension that can then be layered at varying thickness on a substrate.

For example, MOFs for use in mass sensing can be used with quartz crystal microbalances, surface acoustic wave sensors and MEMS cantilevers. Conductometric transducers such as interdigtial electrode transducers can be used or optical transducers such as those comprising an optical path with a source and detector separated by the porous sensing material of the disclosure.

ZIF materials are transparent to light in the region between 2000 and 25000 $cm^{-1}$. $CO_2$ absorbs IR-light in this region. The optical NDIR sensors for $CO_2$ make use of that absorption to quantify the $CO_2$ content of a gas mixture. The ZIF materials can be used as an extra layer to increase the partial pressure of $CO_2$ by adsorption of $CO_2$ in the framework in the optical path of the sensor setup this layer acts as an amplifier (see e.g., Table 1).

TABLE 1

$p(CO_2)$ partial pressure of $CO_2$ in the gas phase; $p'(CO_2)$: virtual partial pressure in the pore system; amplification: $p'(CO_2)/p(CO_2)$;

| $p(CO_2)$/mbar | $p'(CO_2)$/mbar | amplification | $CO_2$/wt % |
|---|---|---|---|
| 3.07 | 47.7 | 155 | 0.01% |
| 30.4 | 461 | 152 | 0.09% |
| 150 | $18.0 \cdot 10^3$ | 120 | 3.30% |
| 298 | $31.2 \cdot 10^3$ | 105 | 5.60% |
| 996 | $70.6 \cdot 10^3$ | 70.6 | 11.8% |

Furthermore the adsorbed gas results in an increase in weight which can be measured by a QCM set up. Due to the high capacity for $CO_2$, this weight increase is larger than for other materials and the uptake is reversible.

The porous materials described herein serve as effective adsorption medium for gas sensing and more particularly $CO_2$ sensing having long term viability and combine two features: (i) a periodic structure for which carbon dioxide uptake and release is fully reversible, and (ii) a flexibility with which chemical functionalization and molecular level fine-tuning can be achieved for optimized uptake capacities.

The analysis of change in sensor composition (e.g., due to binding of an analyte) measured by a change in, for example, resistance, mass or optical properties may be implemented in hardware or software, or a combination of both (e.g., programmable logic arrays and digital signal processors). Unless otherwise specified, the algorithms included as part of the disclosure are not inherently related to any particular computer or other apparatus.

In particular, various general purpose machines may be used with programs written in accordance with the teachings herein, or it may be more convenient to construct more specialized apparatus to perform the operations. However, preferably, the embodiment is implemented in one or more computer programs executing on programmable systems each comprising at least one processor, at least one data storage system (including volatile and non-volatile memory and/or storage elements), at least one input device, and at least one output device. The program code is executed on the processors to perform the functions described herein.

Each such program may be implemented in any desired computer language (including machine, assembly, high level procedural, or object oriented programming languages) to communicate with a computer system. In any case, the language may be a compiled or interpreted language.

Each such computer program is preferably stored on a storage media or device (e.g., ROM, CD-ROM, or magnetic or optical media) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

For example, the computer can be used to measure a signal from the sensor and output an indication of the present of a gas or analyte. In some embodiments, the output may be transmitted to a remote location.

A number of embodiments of the invention have been described. Nevertheless, it will be understood that various modifications may be made without departing from the spirit and scope of the invention. Accordingly, other embodiments are within the scope of the following claims.

What is claimed is:

1. A method of detecting an analyte in a fluid comprising contacting the analyte with a sensor comprising
    a region of a porous framework wherein the region absorbs or adsorbs a gas analyte of interest; and
    a transducer in electrical, mechanical or optical communication with the region that converts an electrical, optical or mass change in the region to a detectable property thereby measuring a gas analyte that absorbs or adsorbs to the region, and
    measuring a change in the detectable property thereby detecting the analyte.

2. The method of claim 1, wherein the analyte is $CO_2$.

3. The method of claim 1, wherein the transducer is an optical, mechanical or electrical transducer.

4. The method of claim 1, wherein the region comprises a metal organic framework (MOF), isoreticular metal organic framework (IRMOF), zeolitic imidazolate framework (ZIF) or covalent organic framework (COF).

5. The method of claim 4, wherein the region comprises a ZIF-68, ZIF-69 or ZIF-70 framework.

6. The method of claim 4, wherein the ZIF comprises the general structure M-L-M, wherein M comprises a transition metal and L is a linking moiety, the linking moiety comprising a structure selected from the group consisting of I, II, III, or any combination thereof:

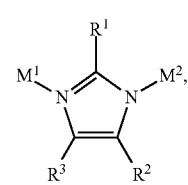

(I)

-continued

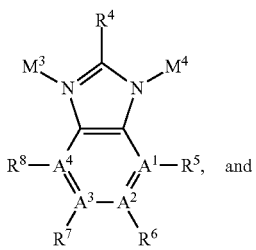
(II)

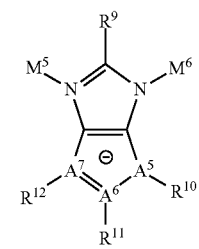
(III)

wherein,
A can be either C or N;
$R^5$-$R^8$ are present when $A^1$ and $A^4$ comprise C;
$R^1$, $R^4$ or $R^9$ comprise a non-sterically hindering group that does not interfere with M; and
$R^2$, $R^3$, $R^5$, $R^6$, $R^7$, $R^8$, $R^{10}$, $R^{11}$, $R^{12}$ are each individually an alkyl, halo, cyano, or nitro,
wherein when the linking group comprises structure III, $R^{10}$, $R^{11}$ and $R^{12}$ are each individually electron withdrawing groups, and
wherein a gas analyte is adsorbed to the zeolitic framework.

7. The method of claim 6, wherein $R^1$, $R^4$ and $R^9$ are individually small group selected from the group consisting of H, methyl, halo, cyano, and ethyl.

8. The method of claim 6, wherein $R^{10}$, $R^{11}$ and $R^{12}$ are each individually selected from the group consisting of a nitro, cyano, fluoro and chloro group.

9. The method of claim 6, wherein L is selected from the group consisting of IV, V, VI, VII, VIII, and IX:

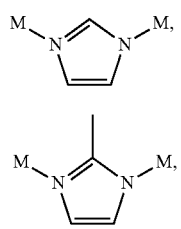
(IV)

(V)

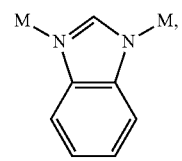
(VI)

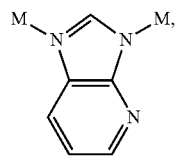
(VII)

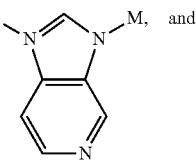
(VIII)

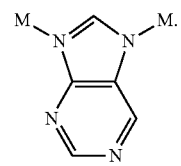
(IX)

10. The method of claim 6, wherein the zeolitic framework comprises a plurality of different transition metals.

11. The method of claim 6, wherein the zeolitic framework comprises a plurality of different linking groups.

12. The method of claim 6, wherein the transition metal is selected from the group consisting of Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg and Uub.

13. The method of claim 6, wherein the transition metal comprises a metal that increases the cationic charge of the zeolitic framework thereby increasing gas selectivity.

14. The method of claim 6, wherein L is an imidazolate or an imidazolate derivative.

15. The method of claim 14, wherein the imidazolate or imidazolate derivative is selected from the group consisting of a substituted imidazolate; a benzimidazolate comprising a methyl, nitro, cyano, or chloro group; an azabenzimidazolate; and an azabenzimidazolte wherein one or two carbon atoms on the benzimidazolate are replaced by nitrogen.

* * * * *

UNITED STATES PATENT AND TRADEMARK OFFICE
CERTIFICATE OF CORRECTION

| | | |
|---|---|---|
| PATENT NO. | : 8,735,161 B2 | Page 1 of 1 |
| APPLICATION NO. | : 13/936315 | |
| DATED | : May 27, 2014 | |
| INVENTOR(S) | : Omar M. Yaghi et al. | |

It is certified that error appears in the above-identified patent and that said Letters Patent is hereby corrected as shown below:

In the Specification

In Column 1, please replace the paragraph at lines 16-23 with the following paragraph:

--STATEMENT REGARDING FEDERALLY SPONSORED RESEARCH OR DEVELOPMENT

This invention was made with Government support under DE-FG02-08ER15935 awarded by the Department of Energy. The Government has certain rights in the invention.--

Signed and Sealed this
Twenty-seventh Day of October, 2015

Michelle K. Lee
*Director of the United States Patent and Trademark Office*